United States Patent
Iezzi et al.

(10) Patent No.: US 7,235,706 B2
(45) Date of Patent: Jun. 26, 2007

(54) PROCESS FOR PREPARING LIGHT OLEFINS BY DEHYDROGENATION OF THE CORRESPONDING PARAFFINS

(75) Inventors: Rodolfo Iezzi, Milan (IT); Andrea Bartolini, Milan (IT); Franco Buonomo, Milan (IT)

(73) Assignees: Snamprogetti S.p.A., Milan (IT); Enitecnologie S.p.A., San Donato Milanese (IT)

( * ) Notice: Subject to any disclaimer, the term of this patent is extended or adjusted under 35 U.S.C. 154(b) by 307 days.

(21) Appl. No.: 10/184,888

(22) Filed: Jul. 1, 2002

(65) Prior Publication Data

US 2002/0198428 A1 Dec. 26, 2002

Related U.S. Application Data

(63) Continuation of application No. 08/895,861, filed on Jul. 17, 1997, now abandoned, which is a continuation of application No. 08/629,080, filed on Apr. 8, 1996, now abandoned, which is a continuation of application No. 08/153,910, filed on Nov. 17, 1993, now abandoned.

(30) Foreign Application Priority Data

Aug. 6, 1993 (IT) .......................... MI93A1792

(51) Int. Cl.
*C07C 5/327* (2006.01)
*C07C 5/333* (2006.01)

(52) U.S. Cl. .................... 585/654; 585/659; 585/661
(58) Field of Classification Search ................ 585/654, 585/659, 661
See application file for complete search history.

(56) References Cited

U.S. PATENT DOCUMENTS

| 3,980,721 A | * | 9/1976 | Juguin et al. ............... 585/430 |
| 4,056,576 A | | 11/1977 | Gregory et al. |
| 4,438,288 A | | 3/1984 | Imai et al. |
| 4,914,075 A | * | 4/1990 | Bricker et al. .............. 502/330 |
| 5,143,886 A | | 9/1992 | Iezzi et al. |
| 5,214,227 A | | 5/1993 | Zhou et al. |
| 5,219,816 A | * | 6/1993 | Zhou et al. .................. 502/223 |
| 5,430,211 A | * | 7/1995 | Pogue et al. ................. 585/323 |
| 5,994,258 A | | 11/1999 | Buonomo et al. |
| 6,362,365 B1 | | 3/2002 | Nezzi et al. |

FOREIGN PATENT DOCUMENTS

| DE | 26 28 282 | | 12/1977 |
| EP | 0637578 B1 | * | 4/1996 |

* cited by examiner

*Primary Examiner*—Tam M. Nguyen
(74) *Attorney, Agent, or Firm*—Oblon, Spivak, McClelland, Maier & Neustadt, P.C.

(57) ABSTRACT

A process for preparing light olefins from corresponding paraffins consists of reacting said paraffins in a reactor, operating at a temperature of between 450 and 800° C., a pressure of between 0.1 and 3 atm absolute and a GHSV of between 100 and 10000 $h^{-1}$, with a catalytic system containing gallium, platinum, possibly one or more alkaline or alkaline-earth metals, and a support consisting of alumina in delta or theta phase or in delta+theta or theta+alpha or delta+theta+alpha mixed phase, modified with silica, the gallium, expressed as $Ga_2O_3$, being in a quantity of between 0.1 and 33.6 wt %, the platinum being in a quantity of between 1 and 99 ppm, the alkaline or alkaline-earth metals, expressed as oxide, being in a quantity of between 0 and 5 wt %, and the silica being in a quantity of between 0.08 and 3 wt %, the rest to 100% being alumina, and regenerating said catalytic system in a regenerator by burning off the coke which has deposited on its surface, without subsequently reducing it.

12 Claims, 1 Drawing Sheet

Figure 1:
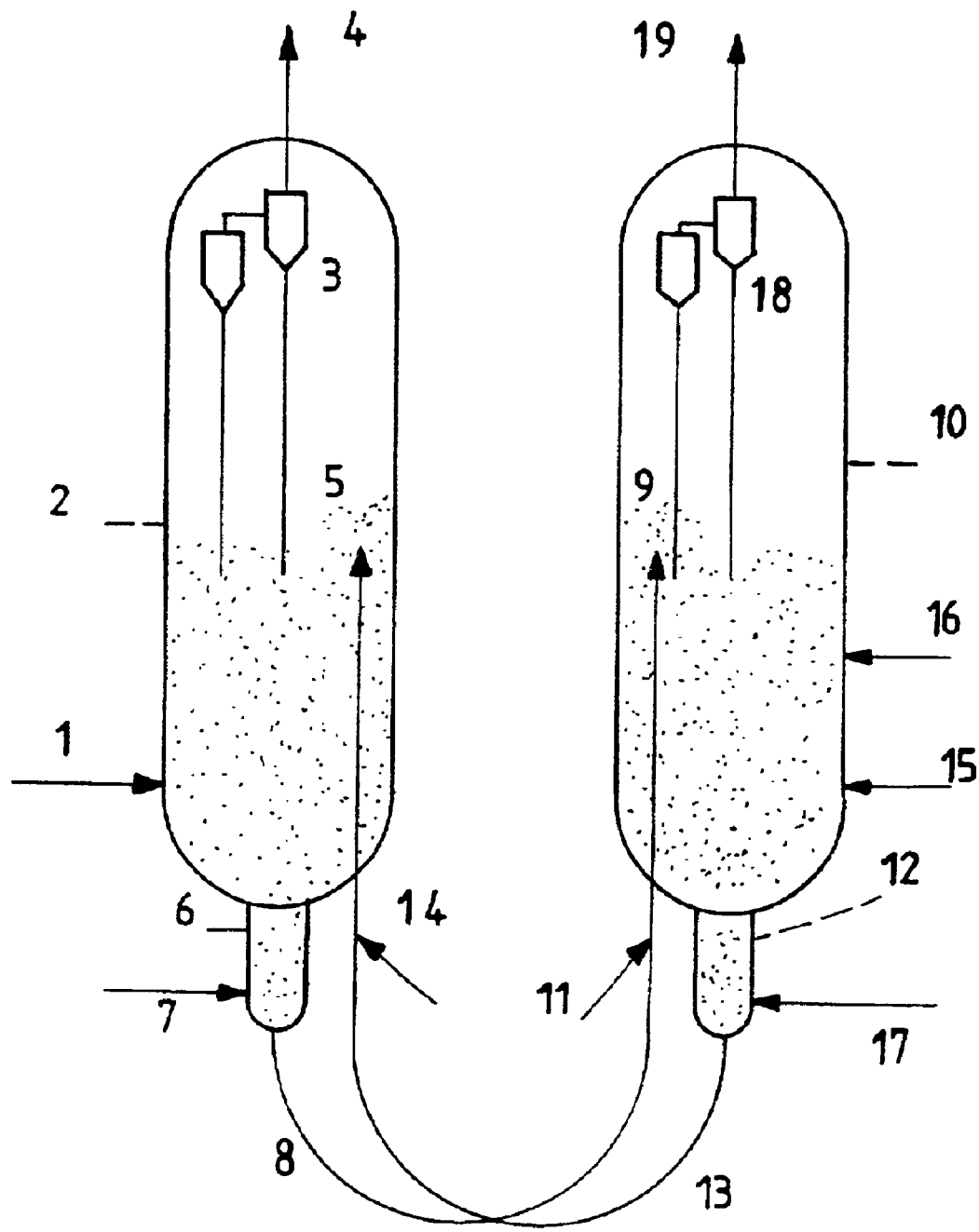

PROCESS FOR PREPARING LIGHT OLEFINS BY DEHYDROGENATION OF THE CORRESPONDING PARAFFINS

This application is a continuation of U.S. application Ser. No. 08/895,861 filed on Jul. 17, 1997, now abandoned, which is a continuation of U.S. application Ser. No. 08/629,080 filed on Apr. 8, 1996, now abandoned, which is a continuation of U.S. application Ser. No. 08/153,910 filed on Nov. 17, 1993, now abandoned.

This invention relates to a process for preparing light olefins by dehydrogenation of the corresponding paraffins, in particular $C_2$–$C_5$ paraffins (paraffins comprising between 2 and 5 carbon atoms). Olefins are important intermediates in the production of chemicals of widespread use, such as polypropylene, antiknock additives (MTBE), high-octane gasolines, alkylated derivatives and numerous other products.

Notwithstanding the growth in the demand for these products, the expansion of industrial processes for their preparation is often limited by the poor availability of olefins, such as isobutene in MTBE production.

This has lead to the identification of other sources of olefin supply in addition to the traditional sources (FCCs, crackers).

Of these, one which is assuming an increasingly important role is the dehydrogenation of light paraffins. This, although stoichiometrically simple, presents both thermodynamic and kinetic problems.

The reaction is endothermic and is controlled by the thermodynamic equilibrium. It requires for example a temperature exceeding 500° C. to dehydrogenate $C_2$–$C_4$ paraffins with economically acceptable conversions per pass. In addition heat must be supplied to the system to satisfy the endothermic requirements of the reaction.

In spite of the high operating temperature the dehydrogenation rate is low, and it is consequently necessary to operate in the presence of a suitable catalyst.

This must be thermally stable and able to ensure high selectivity towards the desired olefin, and in addition minimize isomerization side reactions, cracking, coking and aromatization, and provide industrially useful conversion yields.

The inevitable formation of coke on the catalyst results in progressive reduction in catalytic activity, hence regeneration is periodically necessary.

The formulation must consequently have high stability under both reaction and regeneration conditions.

Numerous attempts have been made to identify catalytic compositions able to satisfy the requirements of this type of process.

In this respect the patent literature describes numerous catalytic compositions both based on noble metals or combinations of these with other chemical species (U.S. Pat. No. 3,531,543; U.S. Pat. No. 4,786,625; U.S. Pat. No. 4,886,928; EP-351067) and based on metal oxides in the presence of promoters, consisting in most cases of supported $Cr_2O_3$ (U.S. Pat. No. 2,945,823; U.S. Pat. No. 2,956,030; U.S. Pat. No. 2,991,255; GB-2162082).

However both these formulation families have drawbacks. Those based on noble metals require special treatment during regeneration (U.S. Pat. No. 4,438,288) to preserve the dehydrogenation activity of the metal species, using for example after-treatment with chlorinated substances followed by reduction. Those based on chromium oxide require high oxide concentrations with consequent environmental problems, which can only be overcome by a certain process complexity. In addition, chromium-based catalysts suffer rapid activity reduction with time if not suitably stabilized.

In recent years numerous patents have been published in which catalytic compositions containing gallium (or gallium compounds) have been used to dehydrogenate paraffins (U.S. Pat. No. 4,056,576) or to aromatize paraffins (AU-509825; AU-565365; U.S. Pat. No. 4,704,494) from which unsaturated compounds are obtained with low conversion and low olefin selectivity.

A patent for dehydrogenating paraffins (U.S. Pat. No. 4,914,075) has also been published which uses catalysts based on noble metals plus gallium. Although not providing numerical information on the performance obtained, this latter patent describes a regeneration procedure typical of a platinum-based catalyst, ie in addition to burning off the deposited coke, halogenated compounds are used for redistributing the metal species followed by reduction of the formulation.

We have surprisingly found that by using a particular catalytic system consisting of gallium or its compounds, a small quantity of platinum chosen within a very defined range, and possibly alkaline or alkaline-earth metals, supported on an alumina modified with silica, we are able to simplify the regeneration stage compared with platinum-based catalysts by eliminating the platinum redispersion and the formulation reduction, while obtaining catalyst performance totally comparable with that obtained from said platinum-based catalytic systems and certainly better than the other catalysts of the aforesaid patents (U.S. Pat. No. 4,056,576; AU-509825; AU-565365; U.S. Pat. No. 4,704,494).

The process for preparing light paraffins from the corresponding paraffins, according to the present invention, consists of reacting said paraffins in a reactor, operating at a temperature of between 450 and 800° C., a pressure of between 0.1 and 3 atm absolute and a GHSV of between 100 and 10000 $h^{-1}$ (normal liters of hydrocarbon/hour per liter of catalyst), with a catalytic system containing gallium, platinum, possibly one or more alkaline or alkaline-earth metals, and a support consisting of alumina in delta or theta phase or in delta+theta or theta+alpha or delta+theta+alpha mixed phase, modified with silica, the gallium, expressed as $Ga_2O_3$, being in a quantity of between 0.1 and 33.6 wt %, preferably between 0.5 and 2.5%, the platinum being in a quantity of between 1 and 99 ppm, preferably between 5 and 50 ppm, the alkaline or alkaline-earth metals, expressed as oxide, being in a quantity of between 0 and 5 wt %, preferably between 0.1 and 1%, and the silica being in a quantity of between 0.08 and 3 wt %, the rest to 100% being alumina, and regenerating said catalytic system in a regenerator by burning off the coke which has deposited on its surface, operating at a temperature exceeding 400° C.

The regeneration is conducted in air and/or oxygen, possibly increasing the temperature of the catalytic system to a suitable value, for example by combustion of a suitable fuel.

Said regeneration does not have to be followed either by catalyst reduction or by redispersion as is normal in the case of platinum-based catalytic systems, in that contrary to the teachings of the known art we have found that reduction produces a negative effect. The fact of not having to effect said reduction results in plant simplification and lower operating costs.

It is advisable to use an alkaline or alkaline-earth metal, preferably potassium, to attenuate the acid properties of the formulation in order to reduce secondary reactions such as cracking, coking, aromatizing and skeletal isomerization.

The surface area of the support should preferably be less than 150 m²/g, determined by the BET method.

The method for preparing the aforedescribed catalytic system consists essentially of dispersing a gallium compound on a support consisting of aluminium (in delta or theta phase or in delta+theta or theta+alpha or delta+theta+alpha mixed phase) and silica.

Some procedures are listed below for dispersing gallium and platinum on the support, the invention however not being limited to these.

The dispersion procedure can consist of impregnating said support with a solution containing gallium or platinum precursors followed by drying and calcining, or by ionic absorption followed by separating the liquid, drying and activating the solid, or by surface adsorption of volatile gallium and platinum species, plus possible calcining of the solid.

Of the aforelisted, the preferred procedures are impregnation by the incipient wetness method, or immersing the support into the solution containing the precursors.

If an alkaline or alkaline-earth metal is used, the following are some procedures for its addition:

coimpregnating the support adding the alkaline metal to the support before dispersing the gallium and platinum precursor treating the solid containing gallium and platinum by ion exchange, impregnation etc. with alkaline metal.

As already stated, the process of the invention is preferably conducted in a fluidized bed system essentially composed of a reactor in which the dehydrogenation reaction takes place, and a regenerator in which the catalyst is regenerated by burning off the coke which has deposited on its surface during the reaction.

The catalyst circulates continuously within the reactor-regenerator system between the reactor and the regenerator, enabling the process to be operated continuously, the heat required for the reaction being provided by the regenerated catalyst, which reaches the reactor at a temperature higher than the mean reaction temperature.

The catalyst is maintained in the fluidized state within the reactor by the reacting gas, which enters the catalytic bed from below via a suitable distribution system.

The reacted gas leaves the reactor from the top after passing through a cyclone system or another system suitable for separating the dust; it can then be fed to a heat exchanger for preheating the feed and then to the separation section where the olefin produced is recovered, whereas the unreacted paraffin can be recycled to synthesis, while the by-products are separated and can be used inter alia in the regenerator as fuel gas.

If an etherification plant is located downstream of the dehydrogenation, the separation section serves only to eliminate its by-products.

In the reactor the catalyst, in the fluidized state, moves in countercurrent to the gaseous phase. It enters the catalytic bed from above through a distributor which distributes it equally over the bed surface, and leaves the reactor from below by passing by gravity into a desorption region, again forming part of the reactor and being of diameter less than or equal to the reaction region, and in which the gas between the particles is shifted and the gas within the particles is desorbed to discharge nitrogen or methane from below, so that the shifted or desorbed gas re-enters the reactor to prevent loss of reactants or product.

The catalyst, still in the fluidized state, is then fed pneumatically to the regenerator.

In the fluidized bed reactor the operating conditions are preferably as follows:

a temperature maintained at between 450 and 650° C., depending on the paraffin or paraffin mixture processed, by regulating the regenerated catalyst flow;

atmospheric or slightly higher than atmospheric pressure;

a space velocity of between 100 and 1000 $h^{-1}$ (N.liters of gas per hour per liter of catalyst), and preferably between 150 and 200;

a catalyst residence time of between 5 and 30 minutes and preferably between 10 and 15 minutes in the fluidized bed region, and between 0.2 and 10 minutes in the desorption region.

Grids with a free area of between 10 and 90% and preferably between 20 and 40% can be arranged horizontally at various heights within the reactor, spaced apart by between 20 and 200 cm.

The purpose of these grids is to prevent the gas and solid remixing so that the gas flow within the reactor approximates to piston flow. This maximizes paraffin conversion and selectivity towards the desired olefin.

The selectivity can be further maximized by the axial temperature profile which becomes established along the bed, with maximum temperature in the top part where the regenerated catalyst arrives and minimum temperature in the bottom part. The temperature difference along the bed is preferably between 15 and 65° C.

The axial temperature profile can also be optimized by distributing the regenerated catalyst at various heights within the catalyst bed.

The pneumatic conveyor system between the reactor and regenerator consists of a conveying line with at least one region in which the catalyst moves with descending movement, preferably maintained in an intermediate condition between minimum fluidization and minimum bubble formation by feeding in a suitable quantity of gas at a suitable height, and a region in which the catalyst moves with ascending movement until it reaches the top of the regenerator catalyst bed by feeding in gas at the base, this substantially reducing the emulsion density.

The regenerator dimensions are preferably similar to those of the reactor.

A suitable diffuser distributes the catalyst from the reactor over the surface of the catalyst bed. Regeneration takes place within the bed by burning off the coke which has deposited on the catalyst, the catalyst being heated by combustion of methane or fuel gas with air, oxygen or another combustion-supporting gas, at a temperature greater than the mean temperature within the reactor.

Before being fed to the reactor, the regenerated catalyst is desorbed of the combustion products.

The gas and solid also move countercurrently within the regenerator. Air is fed into the base of the catalyst bed, the fuel gas being fed in at a suitable height along the bed.

The gas leaving the regenerator, consisting of nitrogen and combustion products, passes through cyclones or a different system in the top part of the apparatus to separate entrained dust, and then after leaving the regenerator is fed to a heat exchanger for preheating the combustion air.

Before discharging to atmosphere the gas passes through a system of filters or other devices to reduce the dust content to a few tenths of a mg per $Nm^3$ of gas.

As the catalytic combustion takes place at a temperature of less than 700° C., the carbon monoxide and nitrogen oxide content of the discharged gases is such as not to require further purification treatment.

The regenerator is preferably operated at atmospheric or slightly higher than atmospheric pressure, at a space velocity of between 100 and 1000 h$^{-1}$, and with a residence time of the solid varying from 5 to 60 minutes, and preferably from 20 to 40 minutes.

The regenerated catalyst is conveyed to the reactor in the same manner in which the spent catalyst is conveyed to the regenerator. The reactor-regenerator system conceived in this manner enables the operating parameters and the performance to be maintained constant during the entire technical life of the plant.

Portions of catalyst are periodically discharged from the system and are replaced with equal portions of fresh catalyst, without ever interrupting plant operation.

The advantages of a fluidized bed reactor-regenerator system can be summarized as follows:

- the optimum temperature profile in the reactor maximizes olefin yield;
- heat is transferred to the reaction directly by the regenerated catalyst. There are no heat transfer surfaces and the strong mixing of the fluidized bed prevents formation of high temperature points which could reduce selectivity;
- the fluidized bed process does not require hydrogen recycling, deleterious from the thermodynamic aspect but essential in other configurations to maintain temperature control;
- all operations take place continuously, it not being necessary to change operating parameters during the entire plant life;
- the plant can be operated with considerable flexibility in terms of actual as against design productivity;
- reaction and regeneration take place in physically separate regions, it being impossible for hydrocarbon streams to mix with oxygen-containing streams;
- the process is conducted at atmospheric or slightly higher than atmospheric pressure. There is therefore no possibility of air infiltration into the reaction region from the outside;
- no special treatment is required to reduce pollutant gas emission.

FIG. 1 shows a possible application of the aforedescribed reactor-regenerator scheme.

The hydrocarbon feed 1 enters the reactor 2 via a suitable distributor (not shown in the figure), the reaction product gas passing through the cyclones 3 to leave the reactor via the line 4. The regenerated catalyst reaches 5 at the top of the catalyst bed and leaves the reactor to pass into the desorber 6 where it comes into contact with the desorbing gas 7. The catalyst then enters the conveying line 8 in which it is conveyed to the regenerator 10 to emerge at the top of the catalyst bed at 9.

In this case a single line is shown for feeding gas into the conveying line, at 11. In this application the conveying line is characterised by having a U-shaped connection between the descending part and ascending part. The catalyst descends along the regenerator, enters the desorber 12, then the conveying line 14 and is conveyed to the reactor. The regeneration air enters at 15, the fuel gas at 16 and the desorbing gas at 17, in each case via suitable distributors (not shown in the figure).

After passing through the cyclones 18 the gas leaves at 19.

Some examples are given hereinafter by way of non-limiting illustration of the present invention.

EXAMPLE 1

A microspheroidal pseudoboehmite with added silica (1.2 wt %) is prepared having a particle diameter of 5–300 μm, by spray-drying a Ludox alumina hydrate and silica sol. A sample of the pseudoboehmite is subjected to thermal treatment consisting of initial calcining at 450° C. for one hour followed by further calcining at 1060° C. for 8 hours in a steam-saturated air stream.

The product obtained has a specific surface of 90 m$^2$/g, a porosity of 0.4 cc/g and consists essentially of delta, theta and alpha transition aluminas.

150 g of this alumina are impregnated, by the incipient wetness procedure, with 60 cc of an aqueous solution containing 6.92 g of $Ga(NO_3)_3 \cdot xH_2O$ (18.9% Ga) in deionized water.

The impregnated substance was left standing for 24 hours at ambient temperature and was then dried at 120° C. for 24 hours. The dried product was finally activated in a dry air stream at 600° C. for 4 hours.

The catalyst composition by weight, for which the gallium is expressed as oxide, is 1.2% $Ga_2O_3$, 1.6% $SiO_2$, balance to 100% $Al_2O_3$.

Its catalytic performance in the dehydrogenation of propane and isobutane by the aforedescribed procedure is reported in Tables 1 and 2.

EXAMPLE 2

150 g of microspheroidal alumina, prepared as described in Example 1, are impregnated by the aforedescribed procedure with an aqueous solution containing 6.90 g of $Ga(NO_3)_3 \cdot xH_2O$ (18.9% Ga) and 1.32 g of an aqueous $H_2PtCl_6$ solution (0.25% Pt) in deionized water. The impregnated substance is treated as described in the preceding example to give a catalyst composed of 1.2% $Ga_2O_3$, 0.002% Pt, 1.6% $SiO_2$, balance to 100% $Al_2O_3$.

Its catalytic performance in the dehydrogenation of propane and isobutane is reported in Tables 1 and 2.

EXAMPLE 3

150 g of microspheroidal alumina, prepared as described in Example 1, are impregnated with an aqueous solution containing 6.92 g of $Ga(NO_3)_3 \cdot xH_2O$ (18.9% Ga) and 0.66 g of an aqueous $H_2PtCl_6$ solution (0.25% Pt) in deionized water. The impregnation and subsequent treatment are conducted as described in Example 1. The resultant catalyst has the following composition: 1.2% $Ga_2O_3$, 0.001% Pt, 1.6% $SiO_2$, balance to 100% $Al_2O_3$.

Its catalytic performance in the dehydrogenation of propane is reported in Table 1.

EXAMPLE 4

150 g of microspheroidal alumina, prepared as described in Example 1, are impregnated with an aqueous solution containing 6.91 g of $Ga(NO_3)_3 \cdot xH_2O$ (18.9% Ga) and 12 g of an aqueous $H_2PtCl_6$ solution (0.25% Pt) in deionized water. The impregnation and subsequent treatment are conducted as described in Example 1. The resultant catalyst has the following composition: 1.2% $Ga_2O_3$, 0.020% Pt, 1.6% $SiO_2$, balance to 100% $Al_2O_3$.

Its catalytic performance in the dehydrogenation of propane is reported in Table 1.

EXAMPLE 5

150 g of microspheroidal alumina, prepared as described in Example 1, are impregnated with an aqueous solution containing 3.51 g of $Ga(NO_3)_3 \cdot xH_2O$ (18.9% Ga) and 1.32 g of an aqueous $H_2PtCl_6$ solution (0.25% Pt) in deionized water. The impregnation and subsequent treatment are conducted as described in Example 1. The resultant catalyst has the following composition: 0.6% $Ga_2O_3$, 0.002% Pt, 1.6% $SiO_2$, balance to 100% $Al_2O_3$.

Its catalytic performance in the dehydrogenation of propane is reported in Table 1.

EXAMPLE 6

150 g of microspheroidal alumina, prepared as described in Example 1, are impregnated by the aforedescribed procedure with an aqueous solution containing 15 g of concentrated HCl, 2 g of $SnCl_2 \cdot 2H_2O$ and 1.21 g of $H_2PtCl_6$ (25% Pt).

The impregnated substance is dried, calcined for 2 hours at 500° C. in air and then reduced for 2 hours at 600° C. in a hydrogen/nitrogen stream.

The catalyst has the following composition:
0.2% Pt, 0.7% Sn, 1.6% $SiO_2$, balance to 100% $Al_2O_3$.

Its catalytic performance in the dehydrogenation of propane and isobutane is reported in Tables 1 and 2.

EXAMPLE 7

150 g of microspheroidal alumina, prepared as described in Example 1, are impregnated with an aqueous solution containing 3.50 g of $Ga(NO_3)_3 \cdot xH_2O$ (18.9% Ga) and 1.50 g of an aqueous $H_2PtCl_6$ solution (10% Pt) in deionized water. The impregnation and subsequent treatment are conducted as described in Example 1. The resultant catalyst has the following composition: 0.6% $Ga_2O_3$, 0.1% Pt, 1.6% $SiO_2$, balance to 100% $Al_2O_3$.

Its catalytic performance in the dehydrogenation of propane is reported in Table 1.

EXAMPLE 8

150 g of microspheroidal alumina, prepared as described in Example 1, are impregnated by the aforesaid procedure with an aqueous solution containing 6.9 g of $Ga(NO_3)_3 \cdot xH_2O$ (18.9% Ga), 0.59 g of $KNO_3$ and 1.32 g of an aqueous $H_2PtCl_6$ solution (0.25% Pt) in deionized water. The impregnated substance is treated as described in the preceding example to give a catalyst having the following composition: 1.2% $Ga_2O_3$, 0.002% Pt, 0,2% $K_2O$, 1.6% $SiO_2$, balance to 100% $Al_2O_3$.

Its catalytic performance in the dehydrogenation of propane and isobutane is reported in Table 1 and Table 2 respectively.

CATALYTIC TESTS

The products of Examples 1–8 are tested in quartz fluidized bed reactors with a porous quartz baffle. The catalytic cycle, simulating the behaviour of an industrial reactor, comprises a reaction stage in which the hydrocarbon is fed (duration 15 minutes), a stripping stage in which nitrogen is passed to free the catalyst of the adsorbed products (10 minutes), and a regeneration stage in which the regeneration gas is fed (oxygen, air or a mixture of the two, usually for 30 minutes). The regeneration and reaction stages are separated from each other by short periods of nitrogen stripping (5 minutes) for safety reasons, as the reaction and regeneration are conducted in the same reactor.

The requirements of the industrial fluidized bed dehydrogenation process advise that regeneration be effected at a temperature exceeding the reaction temperature. In the tests we regenerated at 650° C. whereas the reaction was conducted to 590° C. in the case of propane dehydrogenation and 580° C. in the case of isobutane dehydrogenation.

The reactant space velocity is 400 Nl/lcat.h.

The reactant fed into the reactor is metered by weight.

The effluent from the reactor during the reaction and stripping stages is firstly passed through a cold trap to halt the heavy products for subsequent weight, % carbon and % hydrogen determination, and then collected in a multi-layer sampling bag not related to the particular hydrocarbon species. The bag contents are then measured with a positive displacement pump and analyzed by gas chromatography.

Finally, after stripping for 10 minutes with $N_2$, a catalyst sample is taken to determine the quantity of coke formed. The data obtained are fed into a personal computer to calculate the material balance, conversion and selectivity towards the various products.

From the data of Table 1 the importance of the platinum quantity present in the system can be clearly seen. The performance falls off considerably if platinum is absent (Example 1) or if platinum is present to an extent exceeding 99 ppm (Examples 4, 6 and 7).

Example 2 also shows the negative effect of reduction downstream of the regeneration stage in contrast to the comparative Example 6 in which successive reduction leads to a positive effect.

The reported examples show that the primary catalytic element is gallium, metal or oxide, whereas the platinum acts as a promoter-activator for the primary catalytic species.

Finally, Example 8 shows the capacity of potassium to increase selectivity towards the desired olefin, particularly in the dehydrogenation of isobutane.

TABLE 1

Propane dehydrogenation: catalyst after 150 hours of exposure to the catalytic cycle described in the text.

| Example | $K_2O$ (wt %) | Pt (wt %) | $Ga_2O_3$ (wt %) | Conv. (%) | Sel. (mol %) | Yield (wt) |
|---|---|---|---|---|---|---|
| 1 | — | — | 1.2 | 21 | 79 | 16 |
| 2 | — | 0.002 | 1.2 | 39 | 85 | 32 |
|   |   |   |   | 28* | 84* | 22* |
| 3 | — | 0.001 | 1.2 | 39 | 86 | 32 |
| 4 | — | 0.020 | 1.2 | 30 | 85 | 24 |
| 5 | — | 0.002 | 0.6 | 31 | 88 | 26 |
| 6ç | — | 0.2 | — | 31* | 86* | 25* |
|   |   |   |   | 9 | 89 | 8 |
| 7 | — | 0.10 | 0.6 | 17 | 81 | 13 |
| 8 | 0.18 | 0.002 | 1.2 | 33 | 89 | 28 |

ç 0.7 wt % tin
*after reduction with $H_2$ 650° C.

TABLE 2

Isobutane dehydrogenation: catalyst after 155 hours of exposure to the catalytic cycle described in the text.

| Example | $K_2O$ (wt %) | Pt (wt %) | $Ga_2O_3$ (wt %) | Conv. (%) | Sel. (mol %) i-$C_4H_8$ | Yield (wt) |
|---|---|---|---|---|---|---|
| 1 | — | — | 1.2 | 25 | 59 | 14 |
| 2 | — | 0.002 | 1.2 | 49 | 75 | 35 |

TABLE 2-continued

Isobutane dehydrogenation: catalyst after 155 hours of
exposure to the catalytic cycle described in the text.

| Example | $K_2O$ (wt %) | Pt (wt %) | $GA_2O_3$ (wt %) | Conv. (%) | Sel. (mol %) i-$C_4H_8$ | Yield (wt) |
|---|---|---|---|---|---|---|
| 6ç | — | 0.2 | — | 40* | 64* | 25* |
| 8 | 0.18 | 0.002 | 1.2 | 44 | 86 | 37 |

ç 0.7 wt % tin
*after reduction with $H_2$ 650° C.

What is claimed is:

1. A process for preparing light olefins by dehyrogenation of the corresponding paraffins, consisting of:

reacting said paraffins in a reactor, operating at a temperature ranging from 450 to 800° C., a pressure ranging from 0.1 to 3 atm absolute and a GHSV ranging from 100 to 10000 $h^{-1}$, with a catalytic system containing gallium, platinum, optionally one or more alkali or alkaline earth metals, and a support consisting of alumina in delta or theta phase or in delta+theta or theta+alpha or delta+theta+alpha mixed phase, modified with silica, the gallium, expressed as $Ga_2O_3$, being in a quantity ranging from 0.1 to 33.6 wt %, the platinum being in a quantity ranging from 1 to 99 ppm, the alkali or alkaline earth metals, expressed as oxide, being in a quantity ranging from 0 to 5 wt %, and the silica being in a quantity ranging from 0.08 to 3 wt %, the remainder up to and including 100% being alumina, and regenerating said catalytic system in a regenerator by burning off the coke which has deposited on its surface, operating at a temperature exceeding 400° C.

2. The process as claimed in claim 1, wherein in the catalytic system the gallium, expressed as $Ga_2O_3$, is present in a quantity ranging from 0.5 to 2.5 wt % and the alkali or alkaline earth metals in a quantity ranging from 0.1 to 1 wt %.

3. The process as claimed in claim 1, wherein the alkali metal is potassium.

4. The process as claimed in claim 1, wherein the support has a surface area of less than 150 $m^2$/g, determined by the BET method.

5. The process as claimed in claim 1, wherein the reactor and regenerator are of the fluidized bed type.

6. The process as claimed in claim 5, wherein the dehydrogenation is conducted at a temperature ranging from 450 to 650° C., at atmospheric or slightly higher than atmospheric pressure, at a space velocity ranging from 100 to 1000 $h^{-1}$ and with a catalyst residence time within the fluidized bed region ranging from 5 to 30 minutes.

7. The process as claimed in claim 6, wherein the space velocity ranges from 150 to 200 $h^{-1}$ and the catalyst residence time ranges from 10 to 15 minutes.

8. The process as claimed in claim 5, wherein the regeneration is conducted with air or oxygen or another combustion-supporting gas at a temperature greater than the mean reactor temperature, at atmospheric or slightly higher than atmospheric pressure, at a space velocity ranging from 100 to 1000 $h^{-1}$ and with a solids residence time ranging from 5 to 60 minutes.

9. The process as claimed in claim 2, wherein the alkali metal is potassium.

10. The process as claimed in claim 2, wherein the support has a surface area of less than 150 $m^2$/g, determined by the BET method.

11. The process as claimed in claim 6, wherein the regeneration is conducted with air or oxygen or another combustion-supporting gas at a temperature greater than the mean reactor temperature, at atmospheric or slightly higher than atmospheric pressure, at a space velocity ranging from 100 to 1000 $h^{-1}$ and with a solids residence time ranging from 5 to 60 minutes.

12. The process as claimed in claim 1, wherein the paraffin is a $C_2$–$C_5$-paraffin.

* * * * *